Figure 1:
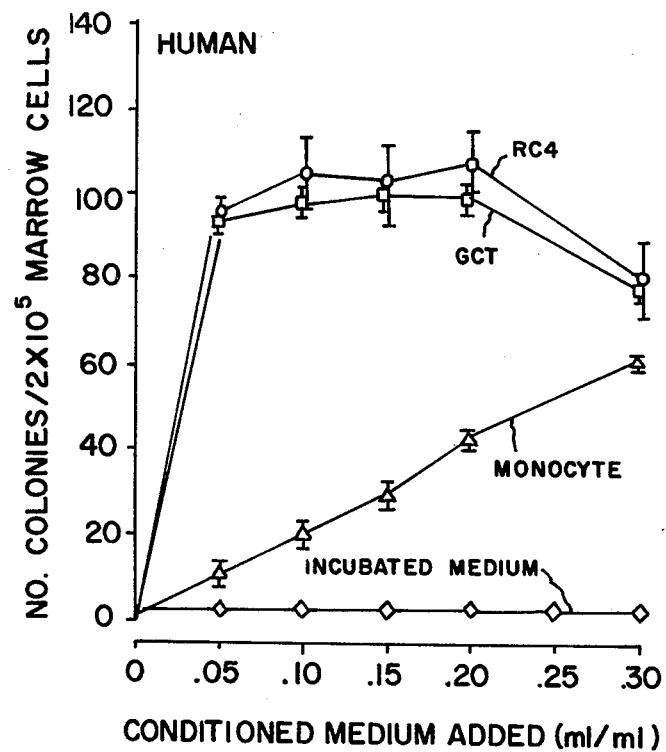

United States Patent [19]  [11]  4,135,975
Lichtman et al.  [45]  Jan. 23, 1979

[54] OBTAINING HUMAN CELL LINES THAT ELABORATE COLONY STIMULATING ACTIVITY FOR MARROW CELLS OF MAN AND OTHER SPECIES AND METHODS OF PREPARING SAME

[76] Inventors: Marshall A. Lichtman; James K. Brennan, both of Rochester, N.Y.

[21] Appl. No.: 860,364

[22] Filed: Dec. 14, 1977

[51] Int. Cl.$^2$ .......................... C12B 3/00; C12K 9/00
[52] U.S. Cl. ...................................................... 195/1.8
[58] Field of Search ......................................... 195/1.8

[56] References Cited

U.S. PATENT DOCUMENTS

| 4,017,361 | 4/1977 | Febvre | 195/1.8 |
| 4,021,302 | 5/1977 | Smith et al. | 195/1.8 |

*Primary Examiner*—Sam Rosen

[57] ABSTRACT

Human cell lines have been obtained which elaborate colony stimulating activity (CSA) for marrow cells, i.e., which enable cells to be grown in vitro for use in bioassay methods in diagnostics and therapy. One cell line, GCT, was obtained from a lung metastasis of a fibrous histiocytoma and another, RC4 from a monocyte enriched fraction of normal blood. These cell lines provide a continuous source of large quantities of conditioned medium from purification of CSA and is more potent in stimulating human narrow growth in vitro than conditioned mediums heretofore available, i.e., human embryo kidney cell or human leukocyte feeder layers, having finite life spans in culture.

8 Claims, 3 Drawing Figures

OBTAINING HUMAN CELL LINES THAT ELABORATE COLONY STIMULATING ACTIVITY FOR MARROW CELLS OF MAN AND OTHER SPECIES AND METHODS OF PREPARING SAME

The present invention relates to cell lines that elaborate colony stimulating activity for marrow cells and methods of preparing same.

We have established two human cell lines which elaborate colony stimulating activity (CSA) for at least four species: man, mouse, rabbit and dog. One, GCT, was isolated from a lung metastasis of a fibrous histiocytoma; the other, RC4, from a monocyte enriched fraction of normal blood. Medium conditioned by either GCT or RC4 cells is more potent in stimulating human marrow growth in vitro than is monocyte conditioned medium or human leukocyte feeder layers.

Fractionation of cell line conditioned medium by Sephacryl S-200 chromatograhy indicates that the maximum activity of the CSA for human marrow cells is eluted within the range of 30,000 to 40,000 daltons. These cell lines provide a continuous source of large quantities of conditioned medium for purification of CSA. Moreover, the invariable growth-supporting activity for all species tested and the high potency of cell-line CSA facilitates studies of its elaboration and biological effects.

Studies in this area which have heretofore been published are set forth in the following references which are enumerated below and are mentioned as the description of our invention proceeds.

1. Stohlman F Jr: Colony-stimulating factor and myelopoiesis. Blood 39:727–732, 1972
2. Golde DW, Cline MJ: Regulation of granulopoiesis. New Engl J Med 291:1388–1395, 1974
3. Greenberg PL, Schrier SL: Clinical utility of in vitro evaluation of granulopoiesis. Ann Rev Med 25:269–278, 1974
4. Boggs DR: Physiology of neutrophil proliferation, maturation and circulation. Clinics in Haematology 4:535–551, 1975
5. McCulloch EA: Granulopoiesis in cultures of human haemopoietic cells. Clinics in Haematology 4:509–533, 1975
6. Robinson WA, Mangalik A: The kinetics and regulation of granulopoiesis. Sem Hem 12:7–25, 1975
7. Stanley ER, Hansen G, Woodcock J. Metcalf D: Colony stimulating factor and the regulation of granulopoiesis and macrophage production. Fed Proc 34:2272–2278, 1975
8. Shadduck RK, Nunna NG: Granulocyte colony stimulating factor. I. Response to acute granulocytopenia. Blood 38:559–568, 1971
9. Morley A, Rickard KA, Howard D, Stohlman F Jr: Studies on the regulation of granulopoiesis. IV. Possible humoral regulation. Blood 37:14–22, 1971
10. Chervenick PA: Effect of endotoxin and post endotoxin plasma on in vitro granulopoiesis. J Lab Clin Med 79:1014–1020, 1972
11. Quesenbery PA, Morley F, Stohlman F Jr., Rickard K, Howard D, Smith M: Effect of endotoxin on granulopoiesis and colony stimulating factor. New Engl J Med 286:277–232, 1972
12. Vogler WR, Mingioli ES, Garwood FA, Smith BA: Granulopoietic stem cell regulators in murine urine: alterations in activity after methotrexate. J Lab Clin Med 79: 379–387, 1972
13. Brown CH III, Carbone PP: In vitro growth of normal and leukemic human bone marrow. J Natl Canc Inst 46:989–1000, 1971
14. Robinson WA, Pike BL: Colony growth of human bone marrow cells in vitro. In Stohlman F Jr (ED): Hemopoietic Cellular Proliferation. New York, Grune and Stratton, 1970, pp 249–259
15. Chervenick PA, Boggs DR: Bone marrow colonies: stimulation in vitro by supernatant from incubated human blood cells. Science 169:691–692, 1970
16. Iscove NN, Senn JS, Till JE, McCulloch EA: Colony formation by normal and leukemic human marrow cells in culture: Effect of conditioned medium from human leukocytes. Blood 37: 1–5, 1971
17. Chervenick, PA, LoBuglio AF: Human blood monocytes: Stimulators of granulocyte and mononuclear colony formation in vitro. Science 178:164–166, 1972
18. Golde DW, Cline MJ: Identification of the colony stimulating cell in human peripheral blood. J Clin Invest 51:2981–2983, 1972
19. Golde DW, Finley TN, Cline MJ: Production of colony-stimulating factor by human macrophages. Lancet 2:1397–1399, 1972
20. Cline MJ, Golde DW: Production of colony stimulating activity by human lymphocytes. Nature 248:703–704, 1974.
21. Baker FL, Broxmeyer HE, Galbraith PR: Control of granulopoiesis in man. III. Inhibition of colony formation by dense leukocytes. J Cell Physiol 86:337–342, 1975
22. Golde DW, Rothman B, Cline MJ: Production of colony stimulating factor by malignant leukocytes. Blood 43:749–756, 1974
23. Brennan JK, Mansky J, Roberts GR, Lichtman MA: Improved methods for reducing calcium and magnesium concentrations in tissue culture medium: Application to studies of lymphoblast proliferation in vitro. In Vitro 11:354–360, 1975
24. Segel GB, Lichtman MA, Gordon BR, MacPherson JL, Nusbacher J: Plateletpheresis residues: A source of large quantities of human blood lymphocytes. Transfusion 16:455–459, 1976.
25. Boyum A: Isolation of mononuclear cells are granulocytes from human blood. Scand J Clin Lab Invest 21:Suppl 97:77, 1968
26. Bennett J, Reed C: Acute Leukemia cytochemical profile: Diagnostic and clinical implications. Blood Cells 1:101–113, 1975.
27. Brennan JK, Lichtman MA, Chamberlain JK, Leblond P: Isolation of variant lymphoma cells with reduced growth requirements for extracellular calcium and magnesium and enhanced oncogenicity. Blood 47:447–459, 1975
28. Yoshida TO, Andersson B: Evidence for a receptor recognizing antigen-complexed immunoglobulin on the surface of activated mouse thymus lymphocytes. Scand J Immunol 1:401–408, 1972
29. Jondal M, Holm G, Wigzell H: Surface markers on human T- and B-lymphocytes forming nonimmune rosettes with sheep red blood cells. J Exp Med 136:207–215, 1972
30. Grammens GL, Brennan JK, Lichtman MA: Inhibitory activity in human marrow directed against mouse marrow proliferation: reduced in subjects with decreased granulopoiesis. Nouv Rev Fr D'Hemat 16:37–46, 1976

31. Epstein AL, Kaplan HS: Biology of the human malignant lymphomas. I. Establishment in continuous cell culture and heterotransplantation of diffuse histiocytic lymphomas. Cancer 34:1851–1872, 1974

32. Sundstrom C, Nilsson K: Establishment and characterization of a human histiocytic lymphoma cell line (U-B7). Int J Cancer 17:565–577, 1976

33. Price GB, Senn JS, McCulloch EA, Till JE: The isolation and properties of granulocytic colony stimulating activities from medium conditioned by human peripheral leucocytes. Biochem J 148:209–217, 1975

34. Price GB, McCulloch EA, Till JE: A new human molecular weight colony stimulating activity. Blood 42:341–348, 1973

35. Austin PE: Studies on conditioning factor activity for marrow cells in culture. Ph D Thesis, University of Toronto, pp 49–58, 1971

36. Walasek OF, Nicol E, Barlow GH: Separation of human and murine granulocyte colony stimulating activity. Fed Proc 35:Abstract No. 1367, 1976

The clonal growth of granulocytic progenitors (CFU-C) in culture requires colony stimulating activity (CSA) (Reviews: See 1-7). In mice, appropriate variations in serum and urinary CSA following perturbation of the granulocytic steady-state suggest that it may have a regulatory function (8-12). To evaluate the role of CSA in human granulopoiesis, a convenient source of large amounts of human CSA is needed. This would facilitate the bioassay of colony forming cells, development of improved methods (e.g. radioimmunoassay) for CSA quantification in human blood and urine and implementation of physiologic studies.

CSA for human marrow is elaborated by human embryo kidney cells (13) and by human leukocytes (14-16), specifically, monocytes (17,18), macrophages (19) and mitogen-stimulated lymphocytes (20). Kidney cells and leukocytes have finite lifespans in culture. Moreover, medium "conditioned" by leukocytes has marked variability in potency. This variability is due, in part, to the admixture with cells that do not elaborate CSA or with cells that release inhibitors of colony growth (21).

Leukemic cells, probably leukemic monocytes, have been shown to release CSA in short term culture (22). We have also observed that cells from acute myelomonocytic leukemia may be a potent source of CSA; however, these cells did not grow for more than a few weeks in culture.

We have otained human cell lines referred to herein as GCT and RC4 by the methods set forth hereinafter. These lines are available at the Animal Tumor Research Facility, University of Rochester Cancer Center, Rochester, N.Y. 14642.

The invention will be more fully understood from a reading of the following description in connection with the accompanying drawings in which:

FIG. 1 is a series of curves showing the following:

Stimulation of human marrow colony growth by cell line or monocyte conditioned medium. Equal numbers of GCT, RC4 and monocytes were cultured in monolayer for four days. Supernatant medium was filtered and assayed for CSA in cultures of normal marrow. Incubated medium without added cells served as a control. To minimize endogenous colony stimulation, the adherent cells of human marrow were removed prior to culture. Colonies were enumerated on day 10. RC4, GCT and monocyte refer to the cells from which the conditioned medium was derived. Data represent the mean ± SE of three experiments.

Figure 2:
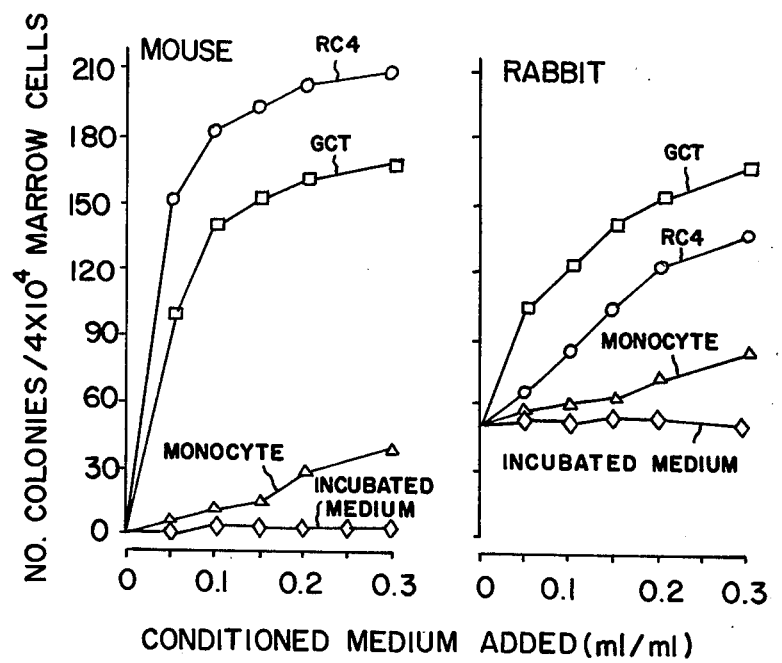

FIG. 2 is a series of curves showing the following:

Mouse and rabbit marrow colony growth by cell line or monocyte conditioned medium. The experiments show the stimulation of mouse and rabbit marrow colony formation by conditioned medium derived from GCT cells, RC4 cells, or monocytes. Adherent marrow cells were not removed prior to culture. In the mouse, endogenous growth is nil, that is, there are no colonies without added conditioned medium. In the rabbit, endogenous growth is present. Colonies were enumerated on day 7.

Figure 3:
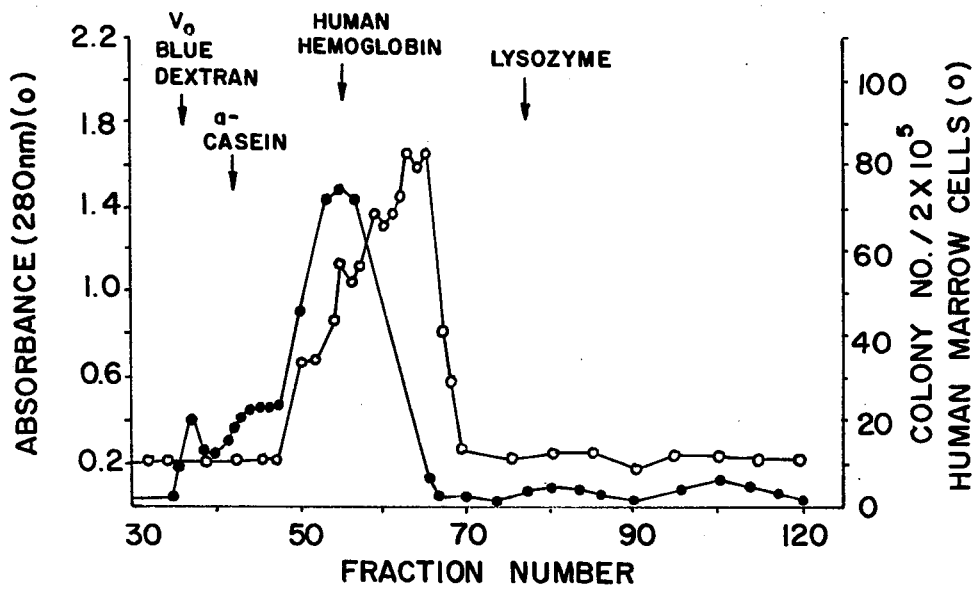

FIG. 3 is another series of curves showing the following:

Elution profile of GCT cell line, human CSA from Sephacryl S-200. GCT conditioned medium was ultrafiltered through a PM 10 membrane. The retentate was applied to an S-200 Sephacryl column equilibrated in phosphate buffered saline at pH 7.4 and eluted with PBS. Five ml fractions of eluate were assayed for CSA using human marrow. The left-side ordinate shows the light absorbance of eluate at 280 nm. The right-side ordinate shows colony number per $2 \times 10^5$ human marrow cells in the presence of 0.2 ml/ml of each fraction. For reference, the elution peaks of blue dextran (molecular weight, $2 \times 10^6$ daltons), α-casein (MW $1.23 \times 10^5$), human hemoglobin (MW, $6.8 \times 10^4$), and lysozyme (MW, $2.4 \times 10^4$) are shown.

The UR-HCL-1 (GCT) cell line was isolated from the lung of a 29-year-old Caucasian male with malignant fibrous histiocytoma. He was in good health until February, 1974 when he presented with a right axillary mass. Physical examination was otherwise normal. Absolute neutropenia (1610–1900 cells/μl), a normal monocyte count (260–300 cells/μl) and a reduced packed cell volume (36–41%) were present. Chest x-ray showed a circumscribed mass on the left lower lobe. An excisional biopsy of the axillary mass revealed malignant fibrous histiocytoma of soft tissue, atypical fibroxanthoma subtype. Neutropenia and anemia persisted. In April, 1974 a left lower lobectomy was performed and the histopathology was reported as the giant cell variant of malignant fibrous histiocytoma. The neutropenia remitted and did not recur. The monocyte count remained normal and anemia persisted. Fourteen months later the patient died of disseminated disease refractory to chemotherapy and radiation. An increase in neutrophil count to 9,000/μl coincident with peritonitis was noted prior to his death. Post mortem examination showed metastases to brain, lung, liver and kidney as well as perforated duodenal ulcer. The spleen and marrow were normal.

UR-HCL-1 (GCT). In April, 1974 when patient M.P. underwent pneumonectomy, a metastatic nodule was removed, minced, and washed in normal saline. Fragments were resuspended in MEM supplemented with 10 percent fetal bovine serum, 100 U penicillin/ml and 100 mcg streptomycin/ml. Five ml aliquots were transferred to 60 × 15 mm tissue culture dishes and cultured at 37° C. in a humidified atmosphere of five percent $CO_2$ in air. Medium exchanges were made at weekly intervals. By the 4th week, cells migrating from fragments had formed a confluent monolayer. Cells removed from dishes by trypsinization were successfully passed in consecutive subcultures. Samples were frozen and stored. For the present studies, thawed cells were adapted to growth in McCoy's 5A medium supplemented with 10 percent fetal bovine serum, penicillin and streptomycin (standard medium).

UR-HCL-1 Clone A (GCT-C). Clone A was obtained by culturing GCT cells in standard medium made viscous by the addition of 1.6 percent w/v methylcellulose (23). A colony was removed under direct vision by means of a micropipet attached to a micromanipulator. The clone was dispersed in 1 ml of standard medium, transferred to a 12 × 75 mm polypropylene tube and cultured. After a cell concentration of $5 \times 10^5$/ml was reached, the suspension was used to seed a larger volume culture. This line is referred to as GCT-C.

The UR-HCL-2 (RC4) line was isolated from the blood of an individual undergoing plateletpheresis at the American Red Cross, Rochester Division, in December 1975. The donor was a healthy 44-year old caucasian female. She had no history of infectious mononucleosis.

UR-HCL-2 (RC4). A residue rich in lymphocytes and monocytes can be obtained as a by-product of plateletpheresis (24). Further enrichment can be achieved by equilibrium density gradient centrifugation in metrizoate-ficoll (25). Monocytes can be separated from lymphocytes by differential adherence to surfaces (25). Combining these procedures yields a cell population comprising >90 percent monocytes (18,25).

Ten ml of residue from the donor J. S. in Medium 199 (M-199) was transferred to a centrifuge tube. Ten ml of 32.8 percent w/v sodium metrizoate:9 percent w/v ficoll (1:2.4 v/v) was injected beneath the cell preparation to create a step-gradient. After centrifugation at $500 \times g$ for 30 minutes at 25° C., the supernatant fraction was removed and the upper third of the metrizoate-ficoll layer harvested into a centrifuge tube containing M-199 at 4° C. Cells were sedimented at 160 + g washed twice in M-199 containing 20 percent fetal calf serum. Approximately 200 ml of cell suspension was transferred to a 250 ml glass bottle, which was then gassed with 7 percent $CO_2$ in air, and tightly capped. Following a 16 hour incubation in a Brunswick shaking water bath (20 oscillations/minute), medium containing non-adherent cells (chiefly lymphocytes) was decanted and the bottle washed with 10 volumes of phosphate buffered saline. Cells adherent to the bottles (chiefly monocytes) were removed by exposure to 4 ml of 0.25 percent trypsin for four minutes, followed by addition of 10 ml of standard medium to stop the action of trypsin and gentle scraping of the bottles with a rubber policeman. The cell suspension was transferred to a centrifuge tube and vortexed to disperse cell clumps. Sufficient standard medium was added to obtain a final concentration of $1 \times 10^6$ cells/ml. Cell viability was >95 percent by dye exclusion. Differential count showed 92 percent monocytes, 8 percent lymphocytes and 2 percent granulocytes. Twenty ml of cell suspension was added to each of two 250 ml tissue culture flasks. The flasks were then incubated at 37° C. in a humidified atmosphere of 8 percent $CO_2$ in air. Medium exchanges were made at weekly intervals. Four weeks after the start of culture, cells, originally rounded and discrete, had become fusiform and syncitial in arrangement. Local islands of proliferation were observed. Two weeks later cultures were divided. Further subcultures were done with decreasing innocula of cells until the line was established.

Maintenance of Cell Lines

GCT, GCT-C and RC4 cells were maintained in standard medium. Subcultures were made at two week intervals by resuspending $5 \times 10^5$ cells in 20 ml of fresh medium and transferring the suspension to 1000 ml tissue culture flasks.

Growth Characteristics of Cells

Monolayer. Cells at $2 \times 10^4$/ml were cultured in replicate $60 \times 15$ mm dishes. At two day intervals, cells from one sample were resuspended and enumerated with a Coulter Model ZBI particle counter with channelizer attachment. Experiments were terminated at two weeks. Doubling time was calculated from the increment in cell number during a 48 hour period of exponential growth.

Colonial growth. Cells at $2 \times 10^4$/ml were suspended in standard medium containing 1.6 percent (w/v) methylcellulose. Three ml were transferred to $60 \times 15$ mm dishes and cultured for 14 days. Colony number was determined with an inverted microscope. Cloning efficiency was expressed as the ratio of colonies to cells cultured.

Morphology, histochemistry, and volume. Exponentially growing cells in monolayer were resuspended to a concentration of $5 \times 10^5$ cells/ml. Samples were : (1) pelleted onto glass slides in a cytocentrifuge and treated with Wright's or histochemical stains (26), (2) prepared for transmission and scanning electron microscopy (27), (3) analyzed for their median volume with a Coulter counter with attached channelizer.

Karyotype. Cells were cultured in the presence of 1.0 $\mu$M colcemide for 8 hours, swollen with 0.075 M KCl for 6 minutes, sedimented onto glass slides and fixed twice with a solution of ethyl alcohol and acetic acid (3:1 v/v). After drying, slides were stained with 2 percent aceto-orcein for 30 minutes and mounted. One hundred consecutive metaphases were examined.

Immunoglobulin secretion. Supernatant media from exponentially growing cell cultures were concentrated over one hundred fold either by ultrafiltration through an Amicon PM 10 filter (nominal exclusion 10,000 daltons) or precipitation with 0–80 percent ammonium sulfate. The concentrate from ultrafiltration and the resuspended precipitate from ammonium sulfate fractionation were tested against rabbit antisera specific for human $\gamma$, $\mu$, $\alpha$, $\lambda$ and $\kappa$ chains utilizing radial immunodiffusion.

Surface receptors. GCT, RC4 or monocytes prepared from plateletpheresis residue were cultured for 48 hours, removed from substratum, and adjusted to equivalent cell concentration ($1 \times 10^6$ cells/ml). Fc receptors were determined as the proportion of cells forming rosettes with sheep erythrocytes coated with anti-sheep erythrocyte antibodies (28). The number of spontaneously rosetting cells were measured by the method of Jondal et al. (29).

Phagocytosis. Cells suspended at $1 \times 10^6$/ml were incubated with an equal volume of $2 \times 10^6$/ml latex particles (2.0 $\mu$m diameter polystyrene or polyvinyl toluene), microbes (E. coli. B. subtilis, N. gonorrhea, C. albicans), and antibody-coated sheep erythrocytes. Samples were removed at intervals of 0 to 120 minutes and cells were examined for ingested particles.

Studies of Colony Stimulating Activity

Preparation of conditioned media. Confluent monolayers ($\sim 1 \times 10^7$ cells) in 1000 ml flasks were continuously cultured in 50 ml of standard medium. Complete medium exchanges were made at four day intervals and the conditioned media were pooled.

Fractionation of conditioned medium. Amicon Diaflo ultrafiltration membranes having exclusion limits of $10^5$ (XM 100), $5 \times 10^4$ (XM 50), $3 \times 10^4$ (PM 30), $1 \times 10^4$ (PM 10) and $5 \times 10^2$ (UM 05) daltons were used to fractionate and concentrate GCT, RC4 and monocyte conditioned medium within certain molecular weight ranges. The retentate from PM 10 ultrafiltration of GCT conditioned medium was applied to a $2.5 \times 10$ cm Sephacryl S-200 column equilibrated in phosphate buffered saline (PBS), pH 7.4, and eluted with PBS at a flow rate of 0.5 ml/min. Blue dextran (molecular weight, $2 \times 10^6$ daltons), α casein (MW, $1.23 \times 10^5$), human hemoglobin (MW, $6.8 \times 10^4$) and ysozyme (MW, $2.4 \times 10^4$) were used as molecular weight markers for standardization of the column.

Assay of conditioned media for CSA. Marrow was obtained from the iliac crest of healthy volunteers and patients undergoing diagnostic aspiration. Nucleated cells were obtained by differential sedimentation at unit gravity (14). For certain experiments adherent marrow cells were removed. Marrow was cultured by a modification of previous methods (15,30). $2 \times 10^5$ non-adherent marrow cells were immobilized in McCoy's 5A medium containing 20% fetal bovine serum, 1.6% (w/v) methylcellulose, antibiotics, and varying concentrations of conditioned or control medium. One ml aliquots were cultured in $35 \times 12$ mm dishes for 10 days. Colonies >50 cells in size were enumerated with an inverted microscope. In certain experiments marrow was also cultured in agar using feeder leukocytes as a source of CSA (14).

Mouse marrow was obtained by flushing the femurs of DBA/2J mice with McCoy's medium. Rabbit marrow was obtained via trocar and resuspended in McCoys's medium. Culture of both was similar to that of human marrow except that: (1) adherent cells were not removed, (2) $4 \times 10^4$ cells/ml were cultured and, (3) the culture interval was 7 days.

Colony Morphology. A micropipet attached to a micromanipulator was filled with 0.05–0.1 ml of standard medium. The micropipet was lowered into a colony using an inverted microscope and the medium slowly injected. Cells loosened from the matrix were aspirated into the pipet, transferred to a glass slide, dried and stained.

Comparison of Monocytes and Cell Lines (Table 1)

Growth. Monocytes did not divide in liquid or semisolid medium. In contrast, GCT and RC4 had doubling times of 55 and 60 hours respectively and a cloning efficiency of 0.2 to 0.5 percent in methylcellulose. Growth in both instances required serum.

Volume. Monocytes had a median volume of 500 $\mu m^3$ which increased to about 1000 $\mu m^3$ following macrophage transformation. GCT and RC4 cells had median volumes of 2000 $\mu m^3$ and 3000 $\mu m^3$.

Karyotype. Monocytes and macrophages were presumably diploid. GCT and RC4 cells had a chromosome number that ranged from 35 to 300 with a modal number of approximately 70 in each line.

Table 1

| Comparison of GCT and RC4 cell Lines to Monocytes | | | |
|---|---|---|---|
| Property | Monocytes | GCT and GCT-C Cells | RC4 Cells |
| Growth | | | |
| Doubling time (h) | — | 55 | 60 |
| Cloning efficiency (%) | — | <0.5 | <0.5 |
| Structure | | | |
| Volume (μm³) | 500 | 2000 | 3000 |
| Chromosome number (modal) | 46 | ~70 | ~70 |
| Surface Receptors | | | |
| SRBC | — | — | — |
| Fc | + | — | — |
| Histochemistry | | | |
| Peroxidase | — | — | — |
| PAS | + | + | + |
| NASDA | + | + | + |
| NASDA + NaF | — | — | — |
| Function | | | |
| Adhesion | + | + | + |
| Phagocytosis | + | — | — |
| IgG Secretion | — | — | — |
| CSA elaboration | + | + | + |

Surface receptors. Neither monocytes nor cell lines formed spontaneous rosettes with sheep erythrocytes whereas 50% of blood lymphocytes formed rosettes. Approximately 90% of monocytes had demonstrable Fc receptors as indicated by rosetting with antibody-coated sheep erythrocytes. Neither cell line formed rosettes with sensitized sheep red cells.

Histochemistry. Monocytes and cell lines were peroxidase negative. All were periodic acid Shiff (PAS) positive; however, staining was more intense and clumped in GCT and RC4 cells. All were stained by Napthol AS-D acetate (NASDA) and the reaction was inhibited by sodium fluoride (NaF) in each. Inhibition by NaF was less in RC4 than in GCT or monocytes.

Adhesion. Monocytes and cell lines adhered and spread on glass and plastic surfaces.

Phagocytosis. Monocytes were able to ingest latex particles, antibody-coated erythrocytes and E coli, B subtilis, N gonorrhea, and C albicans. Greater than 80% of monocytes ingested these particles. Neither GCT nor RC4 cells phagocytized inert particles, sensitized sheep erythrocytes, or microorganisms.

Immunoglobulin secretion. Neither monocytes nor cell lines released immunoglobulins into their culture medium as measured by immunodiffusion techniques.

Elaboration of CSA by monocytes, GCT and RC4 cells. Monocytes, GCT and RC4 cells were incubated at $5 \times 10^5$ cells/ml for four days. Media conditioned by these cells were tested for CSA against human, mouse and rabbit marrow.

Human marrow growth. FIG. 1 depicts the mean and standard error of colony number/$2 \times 10^5$ marrow cells cultured in three separate experiments as the proportion of conditioned media was increased from 0 to 30% (v/v). When medium incubated in the absence of cells was added, no growth was observed. Increasing the proportion of monocyte conditioned medium resulted in a linear increase in colony number to $62 \pm 11$ per $2 \times 10^5$ marrow cells at 30 ml/100 ml. GCT and RC4 conditioned medium stimulated near maximal colony formation ($95 \pm 8$ and $96 \pm 14$) at a concentration of 5 ml/100 ml. At concentrations greater than 20 ml/100 ml of GCT and RC4 conditioned medium colony growth decreased ($84 \pm 4$, $86 \pm 16$).

Animal marrow growth. FIG. 2 illustrates the results of representative experiments in which monocyte or cell line conditioned medium was used to stimulate $4 \times 10^4$/ml mouse or rabbit marrow cells. Cell line conditioned medium stimulated greater colony number than monocyte conditioned medium in these species. The difference is less noticeable in rabbit marrow, perhaps relating to the greater endogenous colony formation in this species. In contrast to human marrow, no inhibition of either mouse or rabbit marrow was noted at higher concentrations of conditioned medium. In experiments not shown, cell line conditioned medium was also found to be more potent than monocyte conditioned medium in stimulating dog marrow.

Comparison of GCT Conditioned Medium and Leukocyte Feeder on Human Marrow Growth GCT conditioned medium was compared to cultures without added CSA and to those stimulated by $1 \times 10^6$ blood leukocytes in the two-layer agar method (14). Marrows from healthy subjects and patients with marrow aplasia, neutropenia, preleukemia and acute leukemia were studied. Adherent cells were not removed prior to culture. As shown in Table 2, GCT conditioned medium was equal to or greater than leukocyte feeder cells in stimulating the growth of normal marrows. In those patients with marrow abnormalities who formed colonies (A.G., D.A., P.C., N.T., and E.L.) GCT conditioned medium stimulated greater growth than leukocyte feeder cells. In one preleukemic patient (R.H.), GCT conditioned medium and leukocyte feeder stimulated only an increase in clusters; however, GCT conditioned medium stimulated a two-fold greater number of clusters. We have not encountered an instance where GCT medium stimulated less growth than leukocyte feeder cells.

Fractionation of Cell Line CSA

We fractionated GCT conditioned medium into various molecular weight ranges by ultrafiltration. All fractions were concentrated five fold and assayed for CSA against human, rabbit and mouse marrow. Table 3 depicts the mean and range of colony number in experiments where marrow cells were stimulated by 20 ml/100 ml of test sample. Unfractionated conditioned medium stimulated 94 human colonies per $2 \times 10^5$ cells, 200 rabbit colonies per $4 \times 10^4$ cells and 310 mouse colonies per $4 \times 10^4$ cells. The XM 100 retentate and that portion of XM 100 filtrate retained by an XM 50 membrane also stimulated colony growth. All fractions derived from the XM 50 filtrate were devoid of CSA. Endogenous cluster or colony formation was inhibited by the PM 10 filtrate-UM 05 retentate. Similar results were obtained with RC4 conditioned medium. Fractions of medium incubated without cells neither stimulated colony formation nor inhibited endogenous cluster formation (not shown). The retention of CSA by an XM 50 ultrafilter suggested that the molecular weight of cell line CSA(s) might be greater than 50,000 daltons. Inhibitory activity in the 500 to 10,000 dalton range was suggested by the absence of cluster formation in cultures containing the PM 10 filtrate-UM 05 retentate. Monocyte CSA was also retained by an XM 50 ultrafilter.

Cascade ultrafiltration provides only a very approximate estimate of molecular size since retention by ultrafilters is a function of molecular shape as well as weight. To further evaluate the molecular nature of cell line CSA, GCT conditioned medium was concentrated by ultrafiltration over a PM10 membrane. Five ml of the retentate was applied to a Sephacryl S-200 column and eluted with PBS. Five ml fractions of the eluate were collected and assayed for activity against human marrow. The results are shown in FIG. 3. The elution fractions in which various molecular weight markers were recovered are indicated. Cell line CSA eluted in a broad peak slightly behind the major protein peak as indicated by absorbance at 280 nm. This protein is primarily fetal bovine albumin since it's quantity can be reduced by affinity chromatography using albumin binding agents and since it corresponds to a DNP-albumin marker. CSA eluted over a molecular weight range of 30,000 to 90,000 daltons. The maximal CSA was observed in elution fraction 63 to 65 which corresponded to a molecular weight of ~ 40,000 daltons. The lower molecular weight limb of the CSA curve was steep, indicating little activity below 35,000 daltons. The higher molecular weight limb was skewed with some activity found up to 90,000 daltons although the bulk of this activity was in the 65,000 dalton region.

Table 2

Comparison of the Effect of GCT Conditioned Medium and Leukocyte Feeder on Human Marrow Growth

| Diagnosis and Subject | Colony number/$2 \times 10^5$ cells | | |
|---|---|---|---|
| | Unstimulated | Leukocyte Feeder | GCT Conditioned Medium (0.15ml/ml) |
| Normal | | | |
| P.R. | 30* | 105 | 110 |
| L.L. | 20* | 87 | 88 |
| J.P. | 10* | 110 | 140 |
| Hypoplasia | | | |
| C.P. (Severe) | 0 | 0 | 0 |
| A.G. (Mild) | 0 | 22 | 32 |
| Neutropenia | | | |
| D.A. (Congenital) | 2* | 17 | 24 |
| P.C. (Congenital) | 2* | 14 | 50 |
| Preleukemia | | | |
| E.C.[1] | 0 | 0 | 0 |
| R.H.[2] | 100* | 450* | 880* |
| N.T.[3] | 2* | 19 | 60 |
| Leukemia | | | |
| B.C. (AML) | 0 | 0 | 0 |
| R.M. (AMML) | 0 | 0 | 0 |
| E.L. (AMoL) | 0 | 30 | 58 |

[1]Refractory sideroblastic anemia with increased myeloblasts
[2]Subsequently died of AML
[3]Subsequently developed AMML
*Clusters (<50 cells)
AML = acute myelogenous leukemia, AMML = acute myelomonocytic leukemia, AMoL = acute monocytic leukemia Table 3

Ultrafiltration of Medium Conditioned by GCT Cells

| Medium Added to Culture (20% v/v) | Human Marrow Colonies/$2 \times 10^5$ cells n=3 | Rabbit Marrow Colonies/$4 \times 10^4$ cells n=2 | Mouse Marrow Colonies/$4 \times 10^4$ cells n=9 |
|---|---|---|---|
| Unfractionated[1] | 94(80–112) | 200(140–260) | 310(160–400) |
| XM 100 Retentate | 102(86–120) | 178(117–240) | 291(145–380) |
| XM 100 Filtrate XM 50 Retentate | 86(70–100) | 137(85–190) | 170(100–210) |
| XM 50 Filtrate XM 30 Retentate | 32*(28–38) | 47(30–65) | 0 |
| PM 30 Filtrate PM 10 Retentate | 22*(10–46) | 32(20–45) | 0 |
| PM 10 Filtrate UM 05 Retentate | 1*(0–5) | 0(0–1) | 0 |
| UM 05 Filtrate[2] | 26*(16–45) | 40(20–60) | 0 |

Table 3-continued

| | Ultrafiltration of Medium Conditioned by GCT Cells | | |
|---|---|---|---|
| Medium Added to Culture (20% v/v) | Human Marrow Colonies/2×10⁵ cells n=3 | Rabbit Marrow Colonies/4×10⁴ cells n=2 | Mouse Marrow Colonies/4×10⁴ cells n=9 |
| Cell Free Incubated Medium | 23*(10–40) | 50(30–70) | 0 |

The data represent the mean and range of three studies.
[1]Desalted and concentrate 5-fold by ultrafiltration against a UM 05 membrane.
[2]Not concentrated
*Clusters (<50 cells)

Several features of GCT and RC4 are similar to monocytes and histiocytes. They exhibit the characteristic histochemical reactions, adhere to surfaces, lack sheep erythrocyte receptors and do not secrete immunoglobulins. Moreover, they elaborate CSA for human marrow, a property associated with human monocytes (17,18) and macrophages (19). Cell line CSA is similar to monocyte CSA in that it supports the growth of all species tested, stimulates granulocyte-monocyte colonies and is retained by an XM 50 ultrafilter.

The morphology (31,32), chromosome number (31), histochemistry (32), and growth rate (31) of GCT and RC4 resemble histiocytic cells from malignant effusions (31,32). GCT and RC4 lack Fc receptors and are not phagocytic. However, only a small proportion of U 937 cells, a presumptive histiocytic line, were found to be phagocytic (32). Moreover, phagocytosis appeared to be lost from GCT cells during passage since they ingested particles immediately after isolation. The normal counterparts of neoplastic cells in culture may not be identified with certainty. For our purposes, the important finding is that GCT and RC4 elaborate CSA in a consistent manner. Their similarity to histiocytes is of interest but does not reflect on their utility as a source of CSA for human and animal marrow growth studies, and for studies of molecular structure of CSA molecules.

Cell line conditioned medium provided a reproducible and potent source of CSA for animal and human marrow. It was more consistent than human blood leukocyte conditioned medium or human blood mononuclear cell conditioned medium. It had a similar potency to leukocyte feeder cells when normal human marrow was studied. In several abnormal marrows, its potency seemed greater than feeder cell systems and, although not shown, mononuclear cell conditioned medium was less potent than the feeder cell system or cell-line CSA sometimes. Thus, cell line CSA may be of critical importance in providing high potency material to assure that clinical studies are being performed in the optimal or near optimal range of the dose-response curve.

The molecular nature of CSA and the possible heterogeneity of CSA in conditioned medium has been studied most intensively by Price and coworkers. In their studies medium conditioned by unfractionated blood leukocytes using ammonium sulfate precipitation, DEAE chromatography, hydroxylapatite adsorption and Sephadex G-150 filtration yielded CSA's for human marrow of ·96,000, 35,000 and 15,000 daltons (33). Chloroformmethanol extraction of ultrafiltered leukocyte conditioned medium yielded an additional CSA of about 1,300 daltons (34). Although unfractionated leukocyte conditioned medium possessed both mouse and human activity (35), purified fractions did not stimulate mouse marrow (33,34). In a preliminary report, Malasek and colleagues have exposed human embryo kidney conditioned medium to PM 10 ultrafiltration, adsorption to calcium phosphate gel and filtration through Sephadex G-75. They isolated a 60,000 to 80,000 dalton CSA which retained mouse activity but had only weak human activity and a 30,000 to 40,000 dalton CSA which stimulated only human colony growth (36).

From the foregoing description it will be apparent that there have been provided new and useful agents for stimulating the growth of the bone marrow of humans and other species, the efficacy of which has been established by clinical data and which is more potent, more reliable and easier to maintain than marrow growth stimulating agents heretofore reported. Methods of fabricating these agents and the depository of the source material therefor have been described.

Variations and modifications in the herein-described agents and methods within the scope of the invention may suggest themselves to those skilled in the art. Accordingly the foregoing description should be taken as illustrative and not in a limiting sense.

What is claimed is:

1. A method for stimulating in-vitro growth of bone marrow cells comprising conditioning a culture media with an active amount of a CSA agent defined as initially obtained from GCT or RC4 cells and their fragments; innoculating the conditioned media with the desired marrow cells; and incubating the resulting modified culture.

2. The method of claim 1 wherein the conditioning CSA agent is initially obtained by culturing a population of human cells obtained from a malignant fibrous histiocytoma, said agent being defined as having a molecular weight of about 30,000-90,000 daltons.

3. The method of claim 1 wherein the CSA agent is initially obtained from a culture by-product of the plateletpheresis of normal human blood, said agent being defined as having a molecular weight of about 30,000-90,000 daltons.

4. The method as set forth in claim 2 wherein said culturing step is carried out with a medium containing fragments of said malignant fibrous histiocytoma, a nutrient, penicillin and streptomycin.

5. The method as set forth in claim 4 wherein said culturing step is carried out in a humidified atmosphere of air and $CO_2$ for a period of time of about four weeks.

6. The method as set forth in claim 3 including the step of enriching said human blood material to obtain a cell population which is rich in monocytes prior to said culturing step, and wherein said culturing step is carried out by incubation in a humidified atmosphere containing $CO_2$ in air.

7. A CSA conditioned medium for growing marrow cells in vitro consisting of a fluid in which a human cell line consisting of cells selected from the group consisting of GCT and RC4 is present and is cultured.

8. The composition as set forth in claim 7 wherein the said medium contains CSA having an eluted molecular weight in the range of 30,000 to 90,000 daltons.

* * * * *